(12) United States Patent
Tiagai et al.

(10) Patent No.: US 12,605,500 B2
(45) Date of Patent: Apr. 21, 2026

(54) ELECTRONIC AUTOMATICALLY ADJUSTING BIDET COMMODE WITH ARTIFICIAL INTELLIGENCE AND SPECTROSCOPY SOFTWARE

(71) Applicant: Smart Hygiene Inc., Marblehead, MA (US)

(72) Inventors: Ilan Tiagai, Marblehead, MA (US); Niloy Choudhury, Newton, MA (US)

( * ) Notice: Subject to any disclaimer, the term of this patent is extended or adjusted under 35 U.S.C. 154(b) by 689 days.

(21) Appl. No.: 18/116,041

(22) Filed: Mar. 1, 2023

(65) Prior Publication Data

US 2024/0293608 A1 Sep. 5, 2024

(51) Int. Cl.
| | |
|---|---|
| *E03D 9/08* | (2006.01) |
| *A61G 5/10* | (2006.01) |
| *A61M 3/02* | (2006.01) |
| *A61M 3/06* | (2006.01) |
| *A61M 35/00* | (2006.01) |

(52) U.S. Cl.
CPC .............. *A61M 3/06* (2013.01); *A61G 5/1002* (2013.01); *A61M 3/0202* (2021.05); *A61M 35/00* (2013.01); *E03D 9/08* (2013.01); *A61M 2205/3303* (2013.01); *A61M 2205/3313* (2013.01); *A61M 2205/3327* (2013.01)

(58) Field of Classification Search
CPC ......... E03D 9/08; A47K 7/04–08; A61M 3/06
See application file for complete search history.

(56) References Cited

U.S. PATENT DOCUMENTS

| | | | | |
|---|---|---|---|---|
| 9,428,898 | B1 * | 8/2016 | Clements | ................. E03D 9/08 |
| 9,822,519 | B2 * | 11/2017 | Hall | ........................... E03D 9/08 |
| 10,357,133 | B2 * | 7/2019 | Okada | .................... A47K 10/34 |
| 10,823,665 | B2 * | 11/2020 | Yan | ......................... G01N 21/31 |
| 2021/0062491 | A1 * | 3/2021 | Cao | ........................... G06T 7/75 |
| 2021/0293013 | A1 * | 9/2021 | Schrant | .................... E03D 9/08 |
| 2022/0213675 | A1 * | 7/2022 | Kramer | ................. H04N 23/56 |

* cited by examiner

*Primary Examiner* — David P Angwin
*Assistant Examiner* — Nicholas A Ros
(74) *Attorney, Agent, or Firm* — Daniel N. Smith

(57) ABSTRACT

A free-standing electronic commode bidet system, a bidet system, and an electronic commode bidet system for insertion onto a wheelchair, all three systems using artificial intelligence and spectroscopy software incorporating fecal detection algorithms. The systems use one or more internal cameras, or other sensors, to capture one or more images of a user as he or she sits on the commode prior to use. The systems automatically detect feces on a user by detecting the absorption spectra of bilirubin, a biomarker of feces. The systems calculate the ratio of green or red light to blue light on an RGB light spectrum. In the presence of bilirubin, more blue light will be absorbed by feces, and the green and red light are not absorbed. Once feces are detected and located on the user, the systems activate one or more water sprays to clean the feces from the user.

20 Claims, 11 Drawing Sheets

ELECTRONIC AUTOMATICALLY ADJUSTING BIDET COMMODE WITH ARTIFICIAL INTELLIGENCE AND SPECTROSCOPY SOFTWARE

FIELD OF THE INVENTION

The field of the invention relates to an electronic commode and bidet systems that uses internal cameras, artificial intelligence, computer vision, and spectroscopy software to automatically detect and clean feces from a user's skin.

BACKGROUND OF INVENTION

Toilets, in general, can be one of the dangerous facilities for those with illnesses, injuries, severe obesity, disabilities, or advanced age. A loss of mobility, strength, and flexibility in the joints makes sitting and standing at the toilet a challenge. Toilets have many slippery surfaces, sharp edges, and involve a lot of motion to utilize correctly.

Using a standard toilet requires one to shift their weight, and move from a seated to standing position, which can cause them to lose their balance quickly. Additionally, many medications and diseases like dementia and Alzheimer's can affect balance, making it even harder for users to control their balance at the toilet. There usually isn't an easily accessible bathroom on the main level of a home, or close to the bedroom for nighttime use.

In addition, cleaning oneself after use of the toilet can be difficult for those with illnesses, injuries, severe obesity, disabilities, or advanced age.

A commode is a type of modified toilet that can be used by someone who needs help due to illness, injury, severe obesity, disability, or advance age. A commode sometimes has wheels to allow easy transport to the bathroom, shower, or other parts of the house. Most commodes have a removable bowl and flip-back armrests. Commodes are a great safety option for older adults because they act as portable toilets and provide the convenience of bringing a toilet to them anywhere in the home, senior care, or health care facility.

Bidet use fluid and air nozzles to wash and dry the genitalia, buttock area, and anus, without the use of any paper tissue using ejected water. Due to the increasing ease of use, functionality, and cleanliness, bidets are being installed in more locations that have multiple users or users with disabilities. Bidets are becoming more common in hospitals because of their utility in maintaining hygiene and their ease of use for disabled or elderly patients. Bidets often make toileting possible for disabled and elderly users, affording them greater opportunity for independence.

The combination of a commode with a bidet, gives maximum usability with maximum cleanliness options.

Accordingly, a need exists for a commode that incorporate bidet for proper cleaning.

SUMMARY OF THE INVENTION

There are additional features of the invention that will be described hereinafter, and which will form the subject matter of the claims appended hereto. In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of the description and should not be regarded as limiting.

The subject invention discloses an electronic commode system with artificial intelligence, computer vision, and spectroscopy software comprising: a re-fillable water reservoir tank; a bowl with an opening; a seat; a seat lid; at least one fluid nozzle for ejecting fluid; means on the commode for moving the fluid nozzle in three-dimensions within the bowl; at least one air dryer comprising an air dryer nozzle and means on the commode for moving the air dryer nozzle in three-dimensions within the bowl; a computing device comprising executable software and a memory storage device; a camera contained within the bowl, wherein the camera is operatively connected to the computing device; a light source within the commode proximate to the camera; at least one actuating device for activating the commode, wherein the activated commode illuminates the genital, anal, and surrounding areas of the buttock regions of a user through the bowl opening with the light source with white light; wherein the camera captures a first plurality of images, or a first video, of the illuminated genital, anal, and surrounding areas of the buttock regions of the user through the bowl opening of the commode, wherein the first plurality of images, or first video, is transmitted to the computing device and analyzed with software to identify feces on the user by detecting the absorption spectra of bilirubin compared to skin of the user in white light; wherein the computing device sends a signal to the means for moving the fluid nozzle in three-dimensions to automatically adjust the nozzle to eject fluid for cleaning any detected feces on the user's genital and rectal areas; wherein the camera captures a second plurality of images, or a second video, of the illuminated genital, anal, and surrounding areas of the buttock regions of the user through the bowl opening of the commode, wherein the second plurality of images, or second video, is transmitted to the computing device and analyzed with software to identify any remaining feces on the user by detecting the absorption spectra of bilirubin compared to skin of the user in white light; wherein the computing device sends a signal to the means for moving the fluid nozzle in three-dimensions to automatically adjust the nozzle to eject fluid for cleaning any detected remaining feces on the user's genital and rectal areas; wherein the camera continues capturing additional pluralities of images, or videos, of the illuminated genital, anal, and surrounding areas of the buttock regions of the user for analysis with the software to identify any remaining feces on the user by detecting the absorption spectra of bilirubin compared to skin of the user in white light until no more feces is identified; and further wherein the computing device sends a signal to the means for moving the air nozzle in three-dimensions to automatically adjust the air nozzles to eject dry air for drying for the user's genital and rectal areas.

The subject invention discloses an electronic bidet system with artificial intelligence, computer vision, and spectroscopy software comprising: a water reservoir tank; a bowl with an opening; a seat; a seat lid; at least one fluid nozzle for ejecting fluid; means on the bidet for moving the fluid nozzle in three-dimensions within the bowl; at least one air dryer comprising an air dryer nozzle and means on the bidet for moving the air dryer nozzle in three-dimensions within the bowl; a computing device comprising executable software and a memory storage device; a camera contained within the bowl, wherein the camera is operatively connected to the computing device; a light source within the bidet proximate to the camera; at least one actuating device for activating the bidet, wherein the activated bidet illuminates the genital, anal, and surrounding areas of the buttock regions of a user through the bowl opening with the light source with white light; wherein the camera captures a first plurality of images, or a first video, of the illuminated genital, anal, and surrounding areas of the buttock regions of the user through the bowl opening of the bidet, wherein the first plurality of images, or first video, is transmitted to the computing device and analyzed with software to identify feces on the user by detecting the absorption spectra of bilirubin compared to skin of the user in white light; wherein the computing device sends a signal to the means for moving the fluid nozzle in three-dimensions to automatically adjust the nozzle to eject fluid for cleaning any detected feces on the user's genital and rectal areas; wherein the camera captures a second plurality of images, or a second video, of the illuminated genital, anal, and surrounding areas of the buttock regions of the user through the bowl opening of the bidet, wherein the second plurality of images, or second video, is transmitted to the computing device and analyzed with software to identify any remaining feces on the user by detecting the absorption spectra of bilirubin compared to skin of the user in white light; wherein the computing device sends a signal to the means for moving the fluid nozzle in three-dimensions to automatically adjust the nozzle to eject fluid for cleaning any detected remaining feces on the user's genital and rectal areas; wherein the camera continues capturing additional pluralities of images, or videos, of the illuminated genital, anal, and surrounding areas of the buttock regions of the user for analysis with the software to identify any remaining feces on the user by detecting the absorption spectra of bilirubin compared to skin of the user in white light until no more feces is identified; and further wherein the computing device sends a signal to the means for moving the air nozzle in three-dimensions to automatically adjust the air nozzles to eject dry air for drying for the user's genital and rectal areas.

The subject invention discloses an electronic wheelchair commode system with artificial intelligence, computer vision, and spectroscopy software comprising: a re-fillable water reservoir tank; a bowl with an opening; a seat; a seat lid; at least one fluid nozzle for ejecting fluid; means on the wheelchair commode for moving the fluid nozzle in three-dimensions within the bowl; at least one air dryer comprising an air dryer nozzle and means on the wheelchair commode for moving the air dryer nozzle in three-dimensions within the bowl; a computing device comprising executable software and a memory storage device; a camera contained within the bowl, wherein the camera is operatively connected to the computing device; a light source within the wheelchair commode proximate to the camera; at least one actuating device for activating the wheelchair commode, wherein the activated wheelchair commode illuminates genital, anal, and surrounding areas of the buttock regions of a user through the bowl opening with the light source with white light; wherein the camera captures a first plurality of images, or a first video, of the illuminated genital, anal, and surrounding areas of the buttock regions of the user through the bowl opening of the wheelchair commode, wherein the first plurality of images, or first video, is transmitted to the computing device and analyzed with software to identify feces on the user by detecting the absorption spectra of bilirubin compared to skin of the user in white light; wherein the computing device sends a signal to the means for moving the fluid nozzle in three-dimensions to automatically adjust the nozzle to eject fluid for cleaning any detected feces on the user's genital and rectal areas; wherein the camera captures a second plurality of images, or second video, of the illuminated genital, anal, and surrounding areas of the buttock regions of the user through the bowl opening of the wheelchair commode, wherein the second plurality of images, or second video, is transmitted to the computing device and analyzed with software to identify any remaining feces on the user by detecting the absorption spectra of bilirubin compared to skin of the user in white light; wherein the computing device sends a signal to the means for moving the fluid nozzle in three-dimensions to automatically adjust the nozzle to eject fluid for cleaning any detected remaining feces on the user's genital and rectal areas; wherein the camera continues capturing additional pluralities of images, or videos, of the illuminated genital, anal, and surrounding areas of the buttock regions of the user for analysis with the software to identify any remaining feces on the user by detecting the absorption spectra of bilirubin compared to skin of the user in white light until no more feces is identified; and further wherein the computing device sends a signal to the means for moving the air nozzle in three-dimensions to automatically adjust the air nozzles to eject dry air for drying for the user's genital and rectal areas.

In embodiments of the subject invention, the feces are detected by computing a function of the ratio of green channel light absorbed divided by blue channel light absorbed, wherein the amount of feces increases as the ratio between the green channel light absorbed divided by blue channel light absorbed increases.

In embodiments of the subject invention, the feces are detected by the ratio of green channel light absorbed divided by blue channel light absorbed minus 1, wherein in the absence of feces has a value of zero and the amount of feces increases as the ratio between the green channel light absorbed divided by blue channel light absorbed increases.

In embodiments of the subject invention, the actuating device comprises a proximity sensor that detects the user sitting on the commode or bidet and automatically activates the commode or bidet.

In embodiments of the subject invention, the actuating device comprises a proximity sensor that detects the user sitting on the commode or bidet and automatically activates the commode or bidet, wherein the proximity sensor consists of a group selected from infrared sensors, weight sensors, and motion detection cameras.

In embodiments of the subject invention, the fluids emitted by the fluid nozzle consist of a group selected from the combination of clean water rinses, hypoallergenic liquid soaps, and liquids medications.

In embodiments of the subject invention, the software will identify and locate the anus, testicles, penis, vagina, hair clusters, burn marks, hemorrhoids, birth marks, moles, acne, tumors, and soiled locations of the user.

In embodiments of the subject invention, the term "software" refers to, and includes, executable code algorithms processed by computer systems, and dedicated hardware running Hardware Description Language (HDL) algorithms in Field-Programmable Gate Arrays (FPGA), or Complex Programmable Logic Device (CPLD), or Application-Specific Integrated Circuits (ASIC).

In embodiments of the subject invention, the term "images" refers to a set of one or more digital images that can take many forms including, but not limited to, digital camera images, digital video sequences, or medical scanner images.

In embodiments of the subject invention, the term "computer vision" refers to techniques and methods for acquiring, processing, analyzing, and understanding digital images and videos. These computer vision techniques and methods include, but are not limited to, visual object recognition, object classification, object identification, object detection, image processing, pattern matching, and pattern recognition.

In embodiments of the subject invention, the commode or bidet may further contain a second fluid nozzle for cleaning the fluid discharged from the fluid nozzle onto the user or cleaning the bowl of the commode or bidet.

In additional embodiments of the subject invention, the actuating device for the commode or bidet may be a button, a microphone combined with voice recognition software, a smartphone, a tablet, a touchpad, a remote control, or a multi-point touch screen.

In embodiments of the subject invention, pressing the button would initiate a cleaning cycle comprising a washing stage and a drying stage.

In another embodiment of the subject invention, the button would initiate a cleaning cycle comprising a washing stage for a first predetermined number of seconds.

In further embodiments of the subject invention, the button would initiate a cleaning cycle comprising a washing stage for a first predetermined number of seconds and a drying stage for a second predetermined number of seconds.

In further embodiments of the subject invention, the button would initiate a cleaning cycle comprising a washing stage until the software determined that the areas are sufficiently clean.

In embodiments of the subject invention, the actuating device for the commode or bidet may be two buttons, one for vaginal cleaning, and one for posterior cleaning, wherein pressing either button would initiate a cleaning cycle comprising a washing stage and a drying stage.

In further embodiments of the subject invention, pressing the button for vaginal cleaning would initiate a cleaning cycle of the vaginal area, comprising a washing stage for a first predetermined number of seconds and a drying stage for a second predetermined number of seconds.

In additional embodiments of the subject invention, pressing the button for posterior cleaning would initiate a cleaning cycle of the anus area, comprising a washing stage whose pattern and duration is controlled by the software until it is deemed that the anus area is sufficiently clean. The software will automatically learn to improve the cleaning process over time.

In embodiments of the subject invention, the electronic system of the commode or bidet may be powered by attachment to an electrical line, internal rechargeable batteries, or solar panels.

There have thus been broadly outlined important features of the invention in order that the detailed description thereof that follows may be better understood, and in order that the present contribution to the art may be better appreciated. There are additional features of the invention that will be described hereinafter, and which will form the subject matter of the claims appended hereto. These together with other embodiments of the invention, and with various features of novelty which characterize the invention, are pointed out with particularity in the claims annexed to and formed as part of this disclosure.

The term "substantially" is defined as at least close to (and can include) a given value or state, as understood by a person of ordinary skill in the art. In one embodiment, the term "substantially" refers to ranges within 10%, preferably within 5%, more preferably within 1%, and most preferably within 0.1% of the given value or state being specified.

For a conceptual understanding of the invention and its operational advantages, refer to the accompanying drawings and descriptive matter in which there are preferred embodiments of the invention illustrated. Other features and advantages of the present invention will become apparent from the following description of the preferred embodiment(s), taken in conjunction with the accompanying drawings, which by way of example; illustrate the principles of the invention.

BRIEF DESCRIPTION OF THE DRAWINGS

Advantages of the present invention will be apparent from the following detailed description of exemplary embodiments thereof, which description should be considered in conjunction with the accompanying drawings.

DETAILED DESCRIPTION OF EMBODIMENTS

Figure 1:
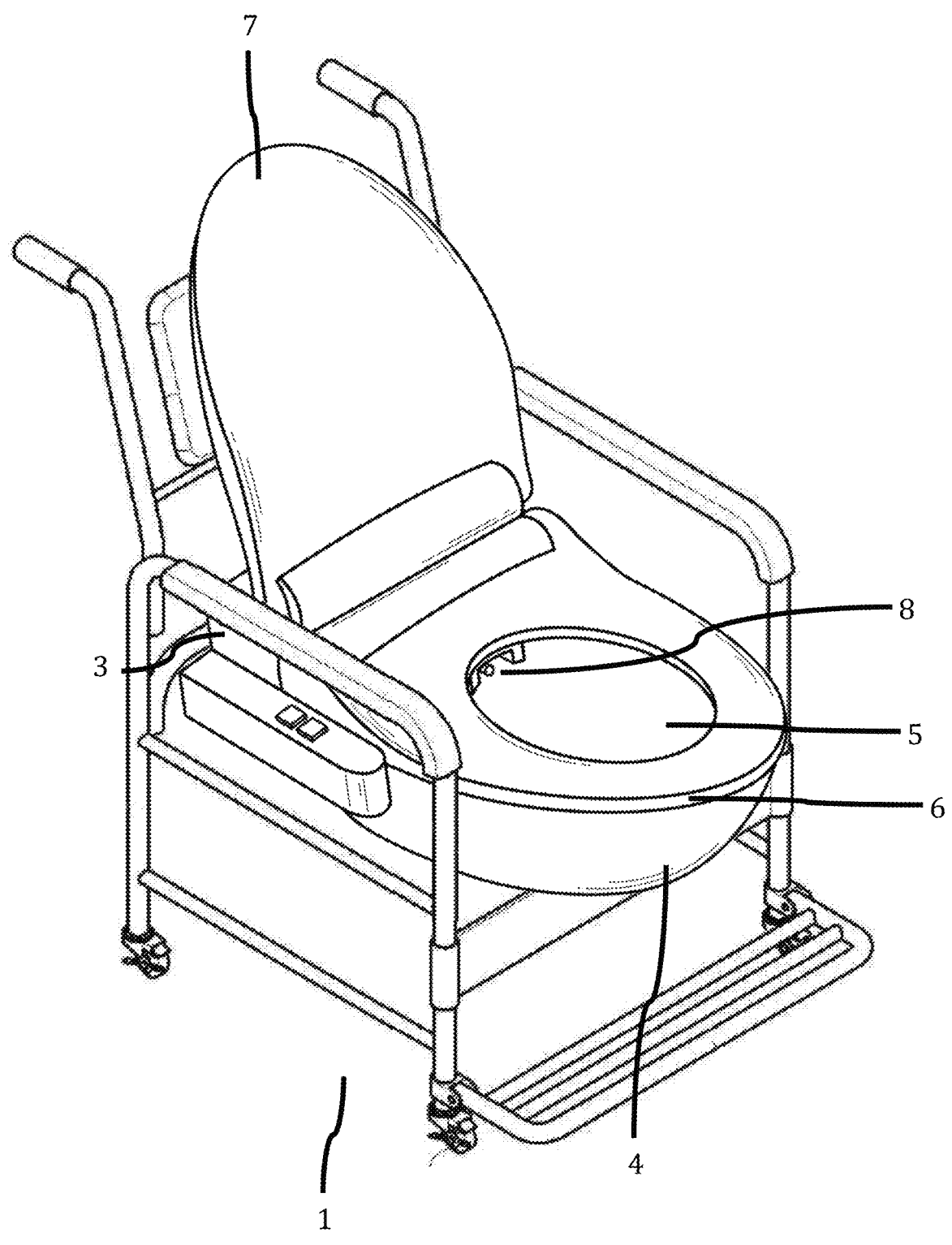
FIG. 1 illustrates a top perspective view of one embodiment of the electronic commode system with the internal camera and fluid nozzle retracted.
Figure 2:
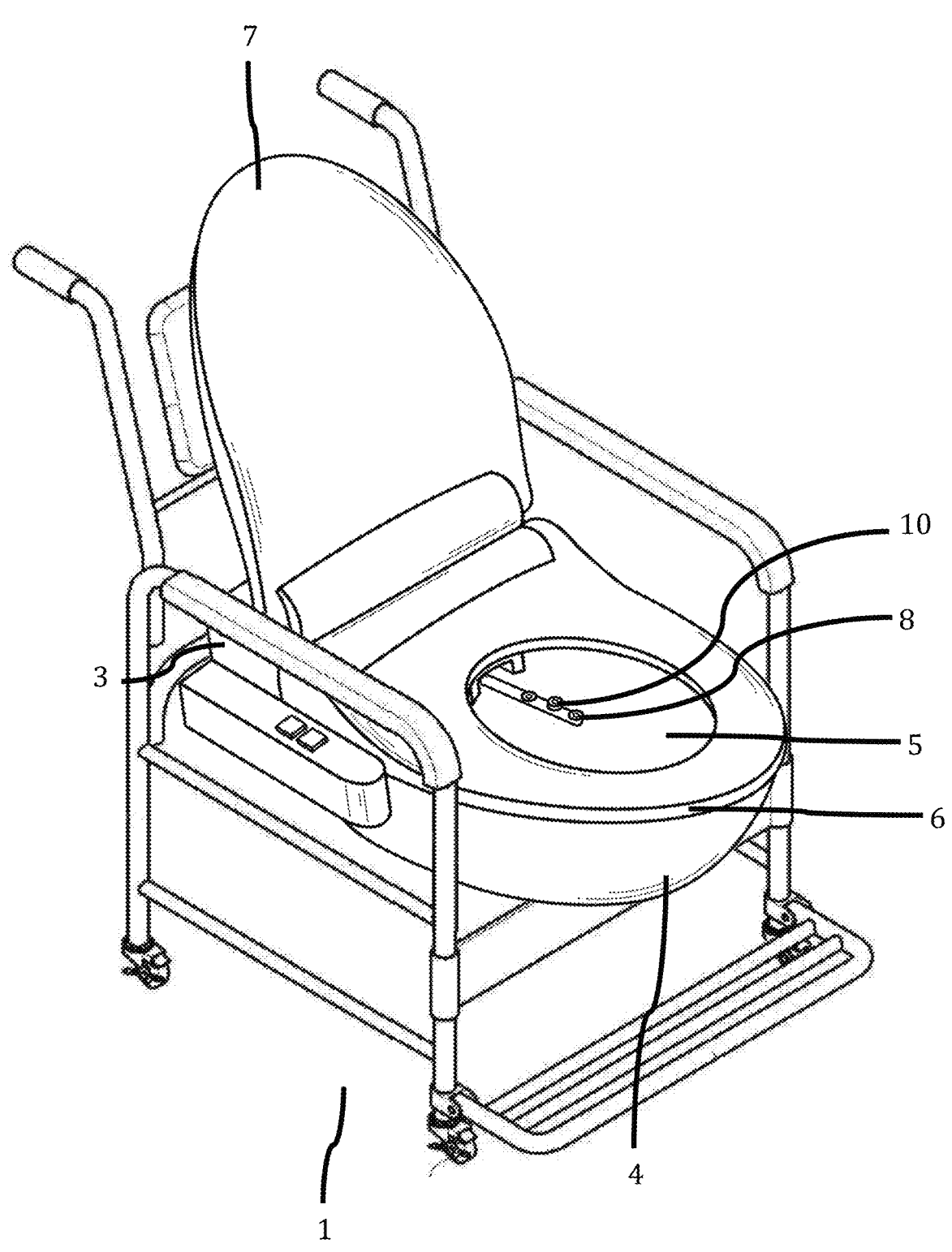
FIG. 2 illustrates a top perspective view of one embodiment of the electronic commode system with the internal camera and fluid nozzle extended.
Figure 3:
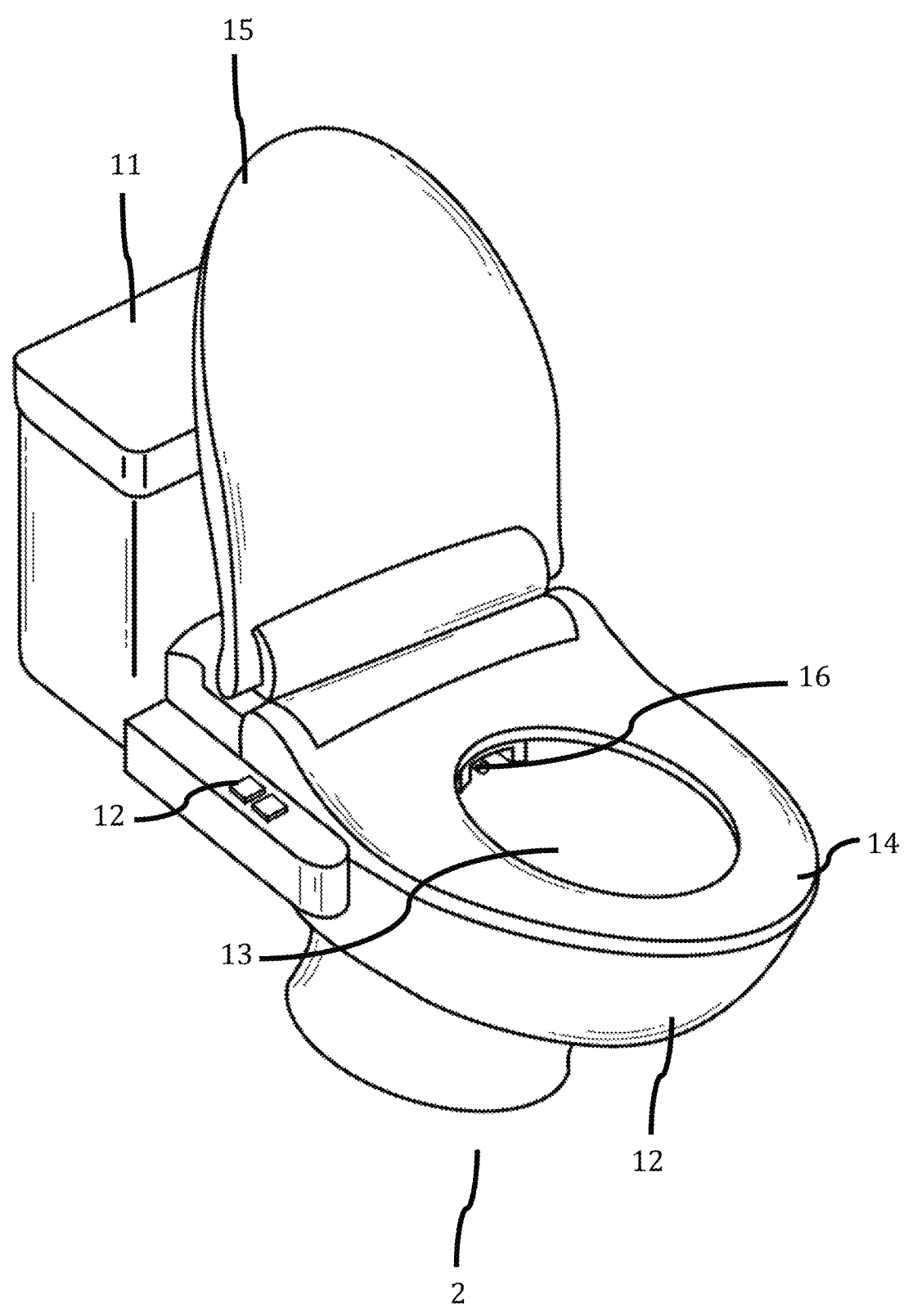
FIG. 3 illustrates a top perspective view of one embodiment of the electronic bidet system with the internal camera and fluid nozzle retracted.
Figure 4:
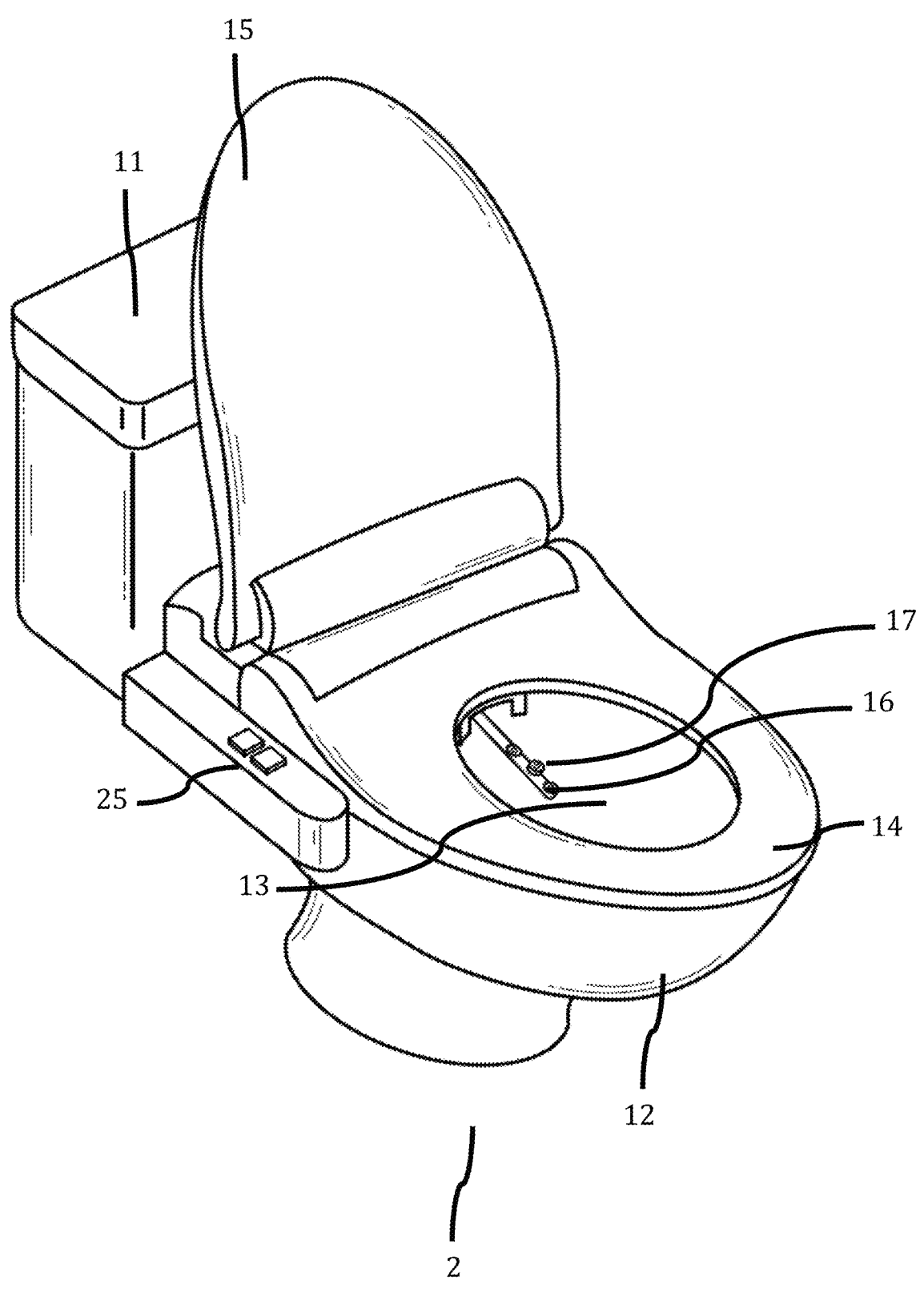
FIG. 4 illustrates a top perspective view of one embodiment of the electronic bidet system with the internal camera and fluid nozzle extended.
Figure 5:
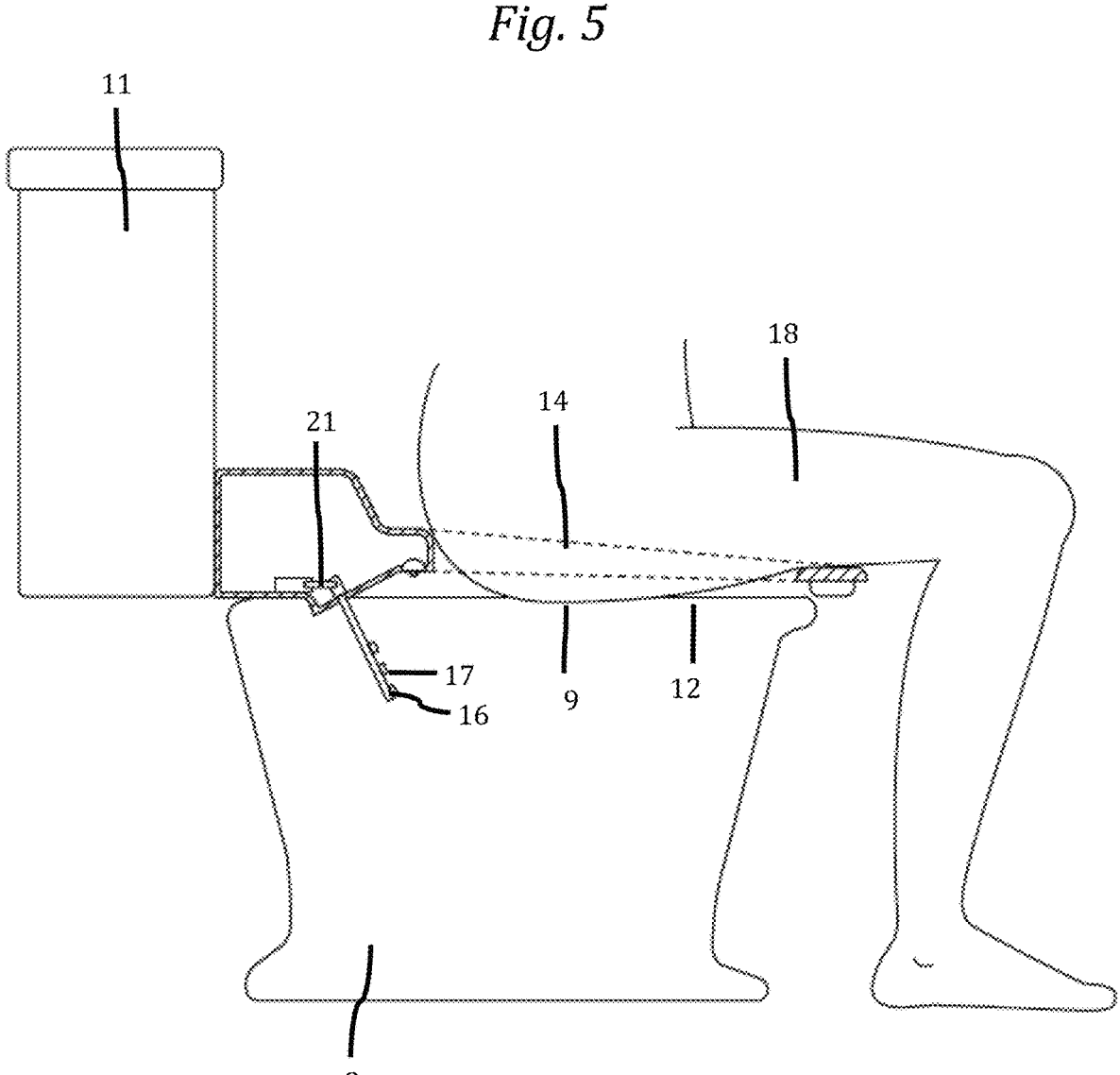
FIG. 5 illustrates a side cross-sectional view of the embodiment of the electronic bidet system with the internal camera and fluid nozzle retracted and a user sitting on the system.

The following will describe, in detail, several embodiments of the present invention. These embodiments are provided by way of explanation only, and thus, should not unduly restrict the scope of the invention. In fact, those of ordinary skill in the art will appreciate upon reading the present specification and viewing the present drawings that the invention teaches many variations and modifications, and that numerous variations of the invention may be employed, used, and made without departing from the scope and spirit of the invention.

As shown in FIGS. 1-11, the subject invention discloses a free-standing electronic commode bidet system 1, a bidet system 2, and an electronic commode bidet system for insertion onto a wheelchair, all three systems using artificial intelligence software incorporating fecal detection algorithms.

The commode 1 system include a re-fillable water tank 3, a bowl 4 with an opening 5, a seat 6, a seat lid 7, at least one fluid nozzle 8 for ejecting water discharged from the water reservoir tank 3 to a user's 18 genital and rectal areas 9, and a housing for an intelligent camera 10. In embodiments of the subject invention, the electronic system of the commode 1 may be powered by attachment to an electrical line, rechargeable batteries, or solar panels. In further embodiments of the subject invention, the re-fillable water tank 3 of the commode 1 does not require connection to a fixed water supply.

The bidet 2 system include a re-fillable water tank 11, a bowl 12 with an opening 13, a seat 14, a seat lid 15, at least one fluid nozzle 16 for ejecting water discharged from the water reservoir tank 11 to a user's 18 genital and rectal areas 9, and a housing for an intelligent camera 17. In embodiments of the subject invention, the electronic system of the bidet 2 may be powered by attachment to an electrical line, rechargeable batteries, or solar panels.

The electronic commode bidet system for insertion onto a wheelchair (not shown) permits the bottom of the wheelchair seat to be detached and folded back. A portable bidet can be inserted from the back of the wheelchair through a sit. The electronic commode bidet system for insertion onto a wheelchair includes a re-fillable water tank, a bowl with an opening, a seat, a seat lid, at least one fluid nozzle for ejecting water discharged from the water reservoir tank to a user's 18 genital and rectal areas 9, and a housing for an intelligent camera. In embodiments of the subject invention, the electronic commode bidet system for insertion onto a wheelchair may be powered by attachment to an electrical line, rechargeable batteries, or solar panels. In embodiments of the subject invention, the re-fillable water tank of the wheelchair commode does not require connection to a fixed water supply.

All the systems of the subject application may also each include a camera flash 19, and an air dryer 20 on the fluid nozzles 8 and 16, respectively. The fluid nozzles 8 and 16 are each connected to means 21 for moving the fluid nozzle and air dryer in three-dimensions within the bowl to change the direction of any ejected water or drying air. The camera light or flash 19 within the bowl 3 provides lighting for capturing images or video when there is no to little light within the bowl (e.g., where the user is very obese and blocks light entering through bowl opening, or a blind user who is using the commode 1 or bidet 2 in the dark).

All the systems of the subject application incorporate one or more intelligent cameras 10 or 17 contained within the bowl, and a controller 22 that can run executable artificial intelligence, computer vision, and spectroscopy software applications.

The intelligent cameras 10 or 17 may each be attached to the fluid nozzle 8 or 16 or to separate air dryer nozzle 23 for moving the air dryer 20 in three-dimensions within the bowl to change the direction of the blown air. The intelligent camera 10 or 17 and camera flash 19 may be connected to a separate nozzle 24 for moving the intelligent camera and flash in three-dimensions within the bowl. The controller 22 further executes software that operatively connects weight or infrared sensors, the fluid nozzles, the means for moving the nozzle in three-dimensions, and the intelligent camera 10 or 17.

A user 18 may activate any of the systems by pressing a button 25, or another actuating device, on the commode 1 or bidet 2, that operatively connected to the controller 22. Embodiments of other actuating devices may include a remote control, a microphone combined with voice recognition software, a smartphone, a tablet, a touchpad, or a multi-point touch screen.

As a user 18 approaches the one of the systems, sensors detect the user 18 and send a signal to the controller 22. In embodiments of the subject inventions, these sensors may be infrared sensors that detect projected infrared light reflected off an approaching user, or weight sensors contained within the seat. In another embodiment of the subject invention, the controller 22 is not activated until the user 18 presses a button 25, or another actuating device.

Once the user 18 sits on the seat of the one of the systems, and the controller 22 is activated, the controller sends a signal to the internal intelligent camera to capture one or more digital images, or a live video feed, of the user's 18 rectal and genital regions 9 through the bowl opening. In a further embodiment of the subject invention, the systems may contain a separate motion detection camera 26 that activates the once a user sits on the seat.

The images, or video feed, are transmitted to the controller 22 and analyzed using artificial intelligence, computer vision, and spectroscopy software to identify and locate lower body orifices in user's 18 genital and rectal areas 9 and their locations, sizes, and shapes. In embodiments of the subject invention, the artificial intelligence software will identify and locate the following categories of objects to be located and tracked: anus, testicles, lower penis, vagina, hair clusters, and various skin disease or conditions, including burn marks, hemorrhoids, birth marks, moles, acne, and tumors. The software will use object models to assign scores or confidences to the category of each detected object on the user's rectal and genital regions. The software will suppress any redundant or conflicting detections.

Feces Detection

Figure 8:
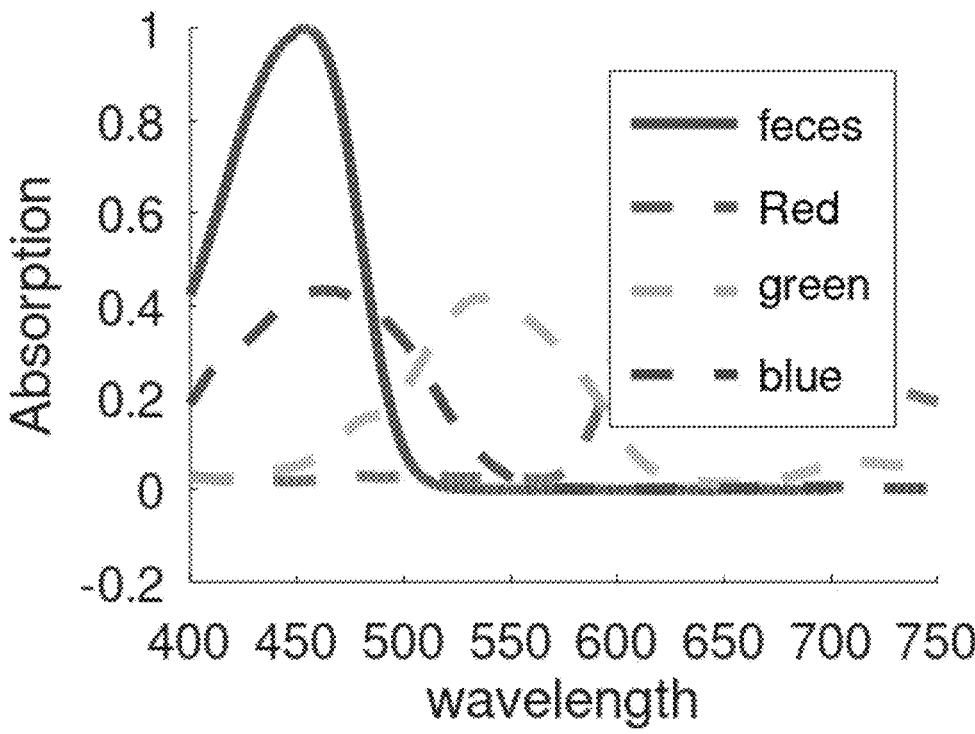
FIG. 8 is a graph illustrating the absorption spectra of bilirubin and the RGB spectra of a typical RGB sensor.

The systems of the subject invention automatically detect feces on a user 18 by detecting the absorption spectra of bilirubin, a biomarker of feces. The absorption spectra of bilirubin and the RGB spectra of a typical RGB sensor is illustrated in FIG. 8.

In the presence of bilirubin, the blue channel (B) will have less light as the blue light gets absorbed by feces, while the green (G) and red (R) light is not absorbed. So, a ratio of green or red channel to blue channel can be a used to detect the presence of feces.

Figure 9:
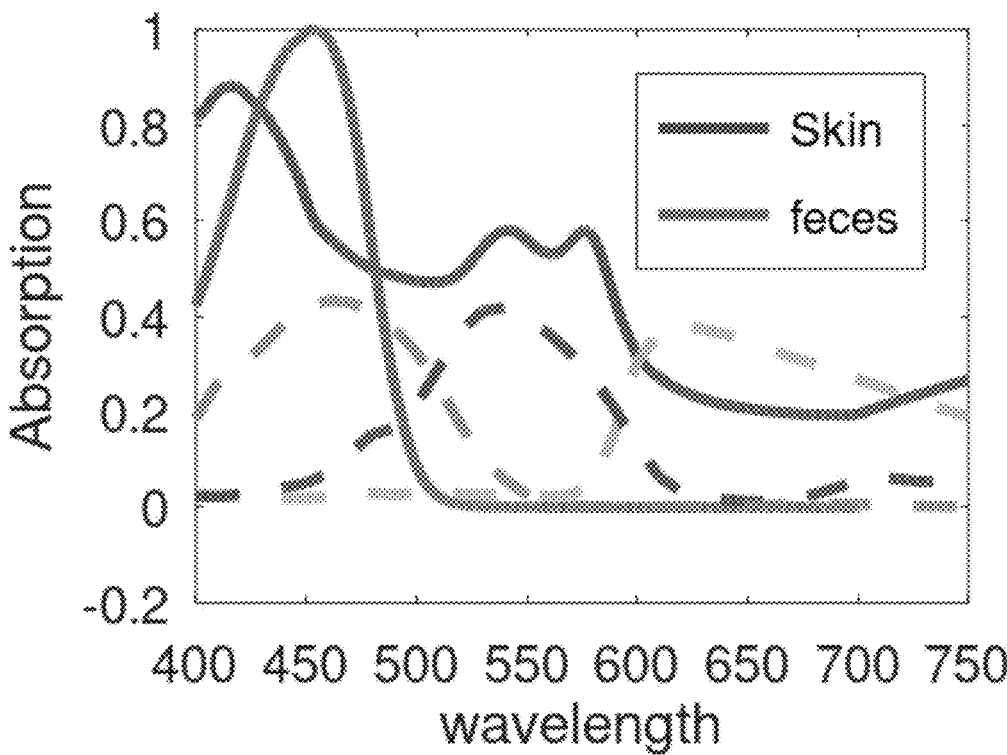
FIG. 9 is a graph illustrating the absorption spectra of human skin, bilirubin, and the RGB spectra of a typical RGB sensor.

FIG. 9 illustrates the absorption spectrum of all colors of skin, bilirubin, and the RGB spectrum of the sensor. The largest contrast between a user's skin color and feces is in the ratio of green to blue channel (G/B). Hence, the detector is:

$$F = \frac{G}{B} - 1$$

Figure 10:
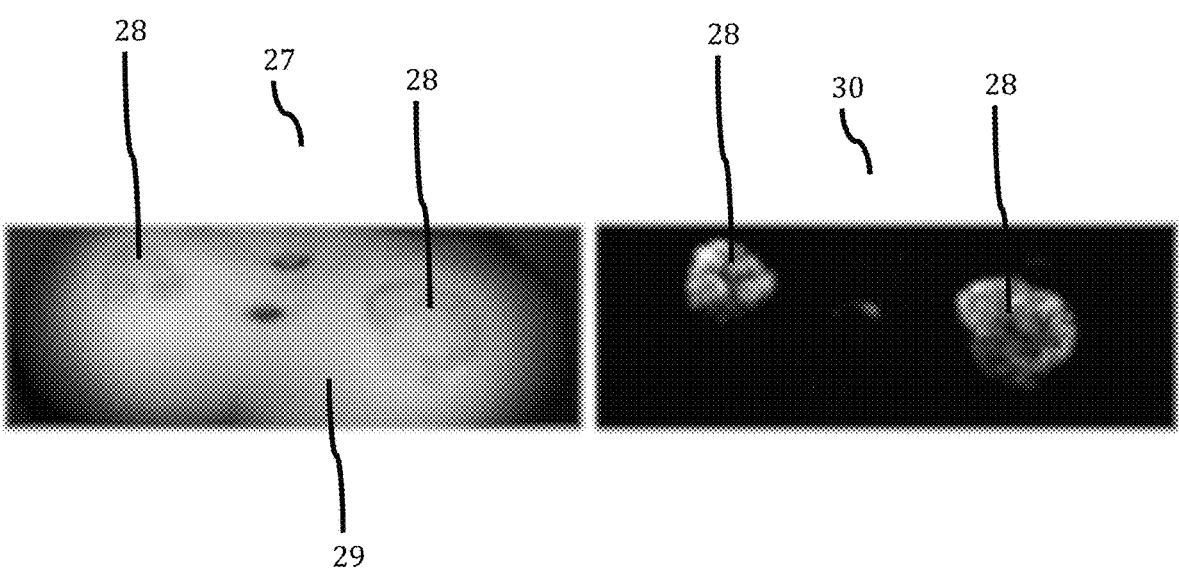
FIG. 10 illustrates an image detection of feces on skin.
Figure 11:
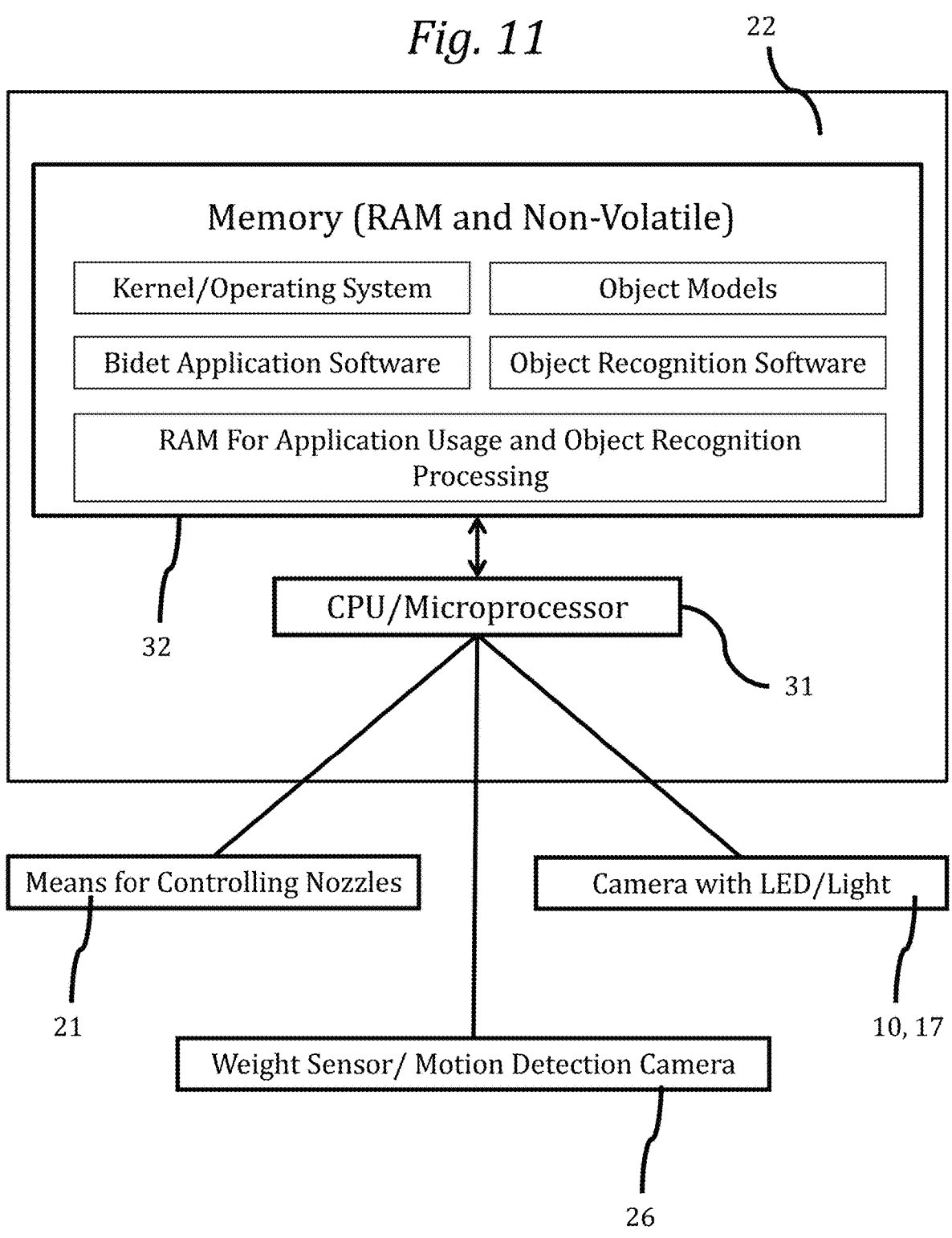
FIG. 11 is a block diagram illustrating a configuration of the electronic bidet system.

FIG. 10 illustrates an example image feces detection. Image 27 is an image of a feces 28 covered skin 29. The feces detection algorithm locates feces soiled skin is identified as shown image 30.

In absence of feces the value of F is zero and F increases as the ratio between G and B increases. However, F is also greater than 1 for unsoiled skin 29. The feces detection algorithm identifies unsoiled skin location and calculates $F_{skin}$ by taking the average value of F in an unsoiled area.

$F_d = F - F_{skin}$ is calculated for the whole image.

The location of skin with feces has a value of $F_d > 0$.

The method of the subject invention detects feces on any type of skin color of the user 18 by detecting the absorption spectra of bilirubin. With any skin color, blue channel (B) will not be absorbed as it is absorbed by feces. Furthermore, the method of the subject invention detects feces around the hair clusters, and various skin disease or conditions, including burn marks, hemorrhoids, birth marks, moles, acne, and tumors of the user 18 by detecting the absorption spectra of bilirubin. With any of these hair clusters, and various skin disease or conditions, blue channel (B) will not be absorbed as it is absorbed by feces.

Based on these analyzed images, the controller 22 sends a signal to the means 21 for moving the fluid nozzle to clean the feces soiled skin. The fluid nozzle will be moved in three-dimensions to automatically adjust the nozzle to eject water to clean for the specific types of orifices, locations of orifices, sizes of orifices, shapes of orifices, gender, body type, weight, and other characteristics of the user.

Once a cleaning cycle has completed, the system will automatically scan the user for remaining feces by detecting the absorption spectra of bilirubin, as outlined above. If remaining feces are detected the system will begin the cleaning cycle again. These steps will be repeated until no feces is detected by the systems.

Once feces are no longer detected on the user, the system will move the air dryer in three-dimensions to automatically adjust the nozzle to dry for the specific types of orifices, locations of orifices, sizes of orifices, shapes of orifices, gender, body type, weight, and other characteristics of the user.

The controller 22 may store the plurality images from each use of the systems. The controller 22 software will use machine learning software to build a model of the user's lower body orifices from the image data. The controller 22 will use this model to improve recognition of the specific user and improve the efficiency of the system for each use by the user.

The controller 22 will use the machine learning software to efficiently clean the user's rectal and genital regions under normal and abnormal circumstances. For example, abnormal circumstances could include, but are not limited to: cleaning the user's anus, when the user has developed hemorrhoids, by using one fluid nozzle to move the hemorrhoid so that another fluid nozzle can clean both sides of the anus; or cleaning the user's rectal and genital regions after diarrhea, where the feces are smeared not only around the anus but around the buttocks, testicles, and genitalia of the user. In case of explosive diarrhea, the controller 22 will clean the bowl by aiming the fluid nozzles at the dirty spots and increase the water pressure until the spots are cleaned.

The controller 22 may also use machine learning software to determine a model of clean user's rectal and genital regions. The controller 22 will continue cleaning until the user's rectal and genital regions are sufficiently clean.

The machine learning software uses computer vision and computational learning theory, to generate a computational model of a user, that can learn from and make predictions on additional data obtained from the user.

In embodiments of the subject invention, the actual computational models and techniques used for the machine learning software include, but are not limited to, supervised learning models such as CNNs (convolutional neural networks), unsupervised semi-supervised learning, reinforcement learning, representation learning, rule-based machine learning, similarity and metric learning, support vector machines, regression algorithms, instance-based algorithms, regularization algorithms, decision tree algorithms, Bayesian algorithms, clustering algorithms, association rule learning algorithms, artificial and traditional neural networks, deep learning algorithms, dimensionality reduction algorithms, ensemble algorithms, random-forest models, traditional stochastic models, and symbolic learning.

In embodiments of the subject invention, the washes emitted by fluid nozzles may comprise any combination of clean water rinses, hypoallergenic liquid soaps, or special liquids medications for diseases or conditions, such as hemorrhoids. In further embodiments, the fluid nozzles may emit appropriate bowl cleaners.

In further embodiments of the subject invention, the controller 22 may direct the fluid nozzles to engage in special cleaning actions for unusual anatomical conditions or physical problems (e.g., hemorrhoids, moles, burn marks, or tumors) that are detected by the computer vision software. The cleaning action can be automatically adjusted for predetermined conditions.

In one embodiments of the subject invention, the system may further include object tracking software to track any movements of the user on the seat. In embodiments of the subject invention, the software will identify and locate the detected objects by category in the captured multiple images. Based on these analyzed images, the controller 22 sends a signal to automatically compensate the nozzles for any movements of the user. In another embodiment of the subject invention, the controller 22 may automatically stop the nozzles when the software detects that the user has begun to move away from seat.

Figure 6:
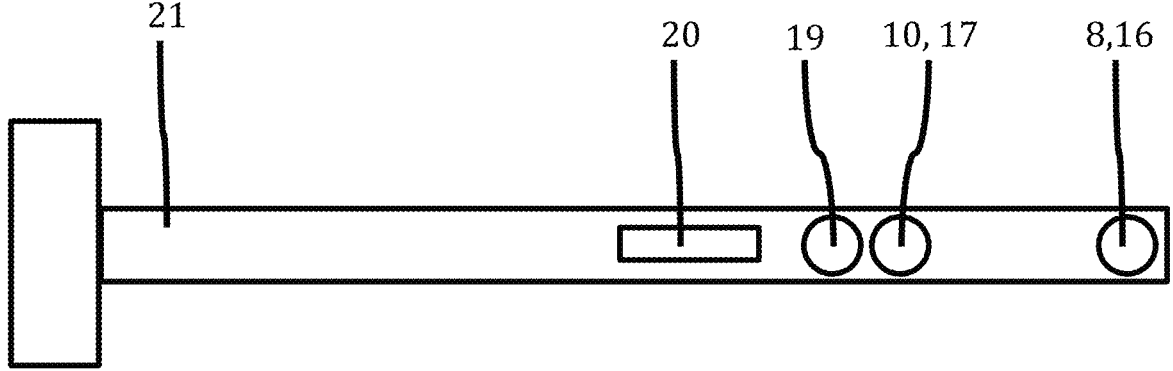
FIG. 6 illustrates a top view of one embodiment of the electronic bidet system with the fluid nozzle which also holds the camera and flash unit, and an air dryer.
Figure 7:
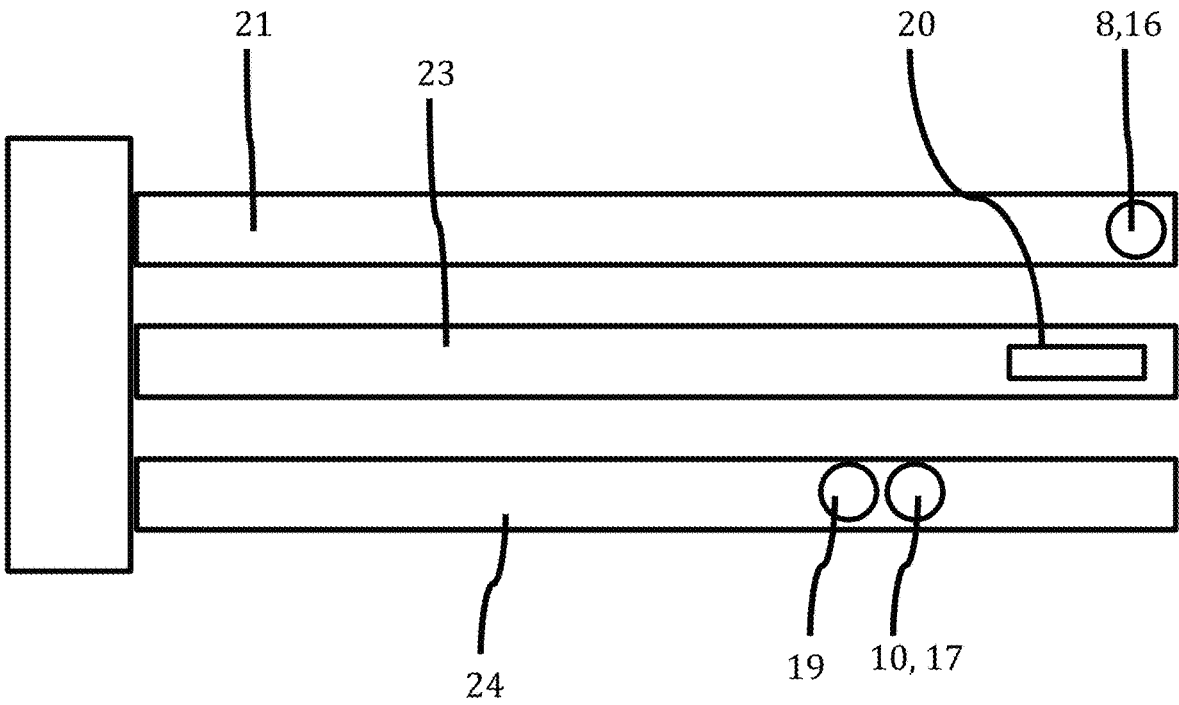
FIG. 7 illustrates a top view of one embodiment of the electronic bidet system with three nozzles. One nozzle to dispense fluid, one nozzle houses the air dryer, and one nozzle to house the camera and flash unit.

FIG. 6 illustrates a block diagram that depicts one embodiment of the controller 22 architecture. The controller 22 may include a CPU/Microprocessor 31, a main RAM/NV memory 32. The CPU/Microprocessor 31 has a capability to interface to the cameras either via a built-in peripheral or an external peripheral through signal communication. This peripheral allows that CPU/Microprocessor 31 to obtain and analyze the images or video captured by the intelligent cameras.

The Memory module 32 may include:

A) a Non-Volatile (NV) Memory to hold the commode application software and machine learning computer vision software to be executed by the CPU/Microprocessor 31 as well a database of models of human body orifices and anatomical conditions (e.g., hemorrhoids) used by the machine learning computer vision software to recognize, classify, detect, localize, segment, and track the lower body orifices and conditions of a user's rectal and genital regions. The Operating system or Kernel may also reside in this NV memory.

B) a Random Access Memory (RAM) needed to process the captured images or video as well as other logic executed by the operating system, machine learning computer vision software, and commode application software.

Embodiments of the CPU/Microprocessor 31 may include processors, microprocessors, DSP, multi-core processors, microcontrollers, system-on-chips, field programmable gate arrays (FPGA), application specific integrated circuits (ASIC), application specific instruction-set processors (ASIP), or graphics processing units (GPU).

In a further embodiment, the main memory 32 may store computer retrievable information and software executable instructions and may also include a solid state, magnetic, or optical recording medium.

In embodiments of the subject invention, the underlying architecture of the system may be implemented using one or more computer programs, each of which may execute under the control of an operating system, such as Windows, OS2, DOS, AIX, UNIX, Linux, or a simple kernel.

The many aspects and benefits of the invention are apparent from the detailed description, and thus, it is intended for the following claims to cover such aspects and benefits of the invention, which fall within the scope, and spirit of the invention. In addition, because numerous modifications and variations will be obvious and readily occur to those skilled in the art, the claims should not be construed to limit the invention to the exact construction and operation illustrated and described herein. Accordingly, all suitable modifications and equivalents should be understood to fall within the scope of the invention as claimed herein.

What is claimed is:

1. An electronic commode system with artificial intelligence, computer vision, and spectroscopy software comprising:

a re-fillable water reservoir tank;

a bowl with an opening;

a seat;

a seat lid;

at least one fluid nozzle for ejecting fluid;

means on the commode for moving the fluid nozzle in three-dimensions within the bowl;

at least one air dryer comprising an air dryer nozzle and means on the commode for moving the air dryer nozzle in three-dimensions within the bowl;

a computing device comprising executable software and a memory storage device;

a camera contained within the bowl, wherein the camera is operatively connected to the computing device;

a light source within the commode proximate to the camera;

at least one actuating device for activating the commode, wherein the activated commode illuminates the genital, anal, and surrounding areas of the buttock regions of a user through the bowl opening with the light source with white light;

wherein the camera captures a first plurality of images of the illuminated genital, anal, and surrounding areas of the buttock regions of the user through the bowl opening of the commode, wherein the first plurality of images is transmitted to the computing device and analyzed with software to identify feces on the user by detecting the absorption spectra of bilirubin compared to skin of the user in white light;

wherein the computing device sends a signal to the means for moving the fluid nozzle in three-dimensions to automatically adjust the nozzle to eject fluid for cleaning any detected feces on the user's genital and rectal areas;

wherein the camera captures a second plurality of image of the illuminated genital, anal, and surrounding areas of the buttock regions of the user through the bowl opening of the commode, wherein the second plurality of images is transmitted to the computing device and analyzed with software to identify any remaining feces on the user by detecting the absorption spectra of bilirubin compared to skin of the user in white light;

wherein the computing device sends a signal to the means for moving the fluid nozzle in three-dimensions to automatically adjust the nozzle to eject fluid for cleaning any detected remaining feces on the user's genital and rectal areas;

wherein the camera continues capturing additional pluralities of images of the illuminated genital, anal, and surrounding areas of the buttock regions of the user for analysis with the software to identify any remaining feces on the user by detecting the absorption spectra of bilirubin compared to skin of the user in white light until no more feces is identified; and

12 further wherein the computing device sends a signal to the means for moving the air nozzle in three-dimensions to automatically adjust the air nozzles to eject dry air for drying for the user's genital and rectal areas.

2. The electronic commode system of claim 1, wherein feces are detected by the ratio of green channel light absorbed divided by blue channel light absorbed minus 1, wherein in the absence of feces has a value of zero and the amount of feces increases as the ratio between the green channel light absorbed divided by blue channel light absorbed increases.

3. The electronic commode system of claim 1, wherein the actuating device comprises a proximity sensor that detects the user sitting on the commode and automatically activates the commode.

4. The electronic commode system of claim 1, wherein the actuating device comprises a proximity sensor that detects the user sitting on the commode and automatically activates the commode wherein the proximity sensor consists of a group selected from infrared sensors, weight sensors, and motion detection cameras.

5. The electronic commode system of claim 1, wherein the fluids emitted by the fluid nozzle consist of a group selected from the combination of clean water rinses, hypoallergenic liquid soaps, and liquids medications.

6. The electronic commode system of claim 1, wherein the software will identify and locate the anus, testicles, penis, vagina, hair clusters, burn marks, hemorrhoids, birth marks, moles, acne, tumors, and soiled locations of the user.

7. The electronic commode system of claim 1, wherein the first, second, and additional pluralities of images comprise digital video.

8. An electronic bidet system with artificial intelligence, computer vision, and spectroscopy software comprising:

a water reservoir tank;

a bowl with an opening;

a seat;

a seat lid;

at least one fluid nozzle for ejecting fluid;

means on the bidet for moving the fluid nozzle in three-dimensions within the bowl;

at least one air dryer comprising an air dryer nozzle and means on the bidet for moving the air dryer nozzle in three-dimensions within the bowl;

a computing device comprising executable software and a memory storage device;

a camera contained within the bowl, wherein the camera is operatively connected to the computing device;

a light source within the bidet proximate to the camera;

at least one actuating device for activating the bidet, wherein the activated bidet illuminates the genital, anal, and surrounding areas of the buttock regions of a user through the bowl opening with the light source with white light;

wherein the camera captures a first plurality of images of the illuminated genital, anal, and surrounding areas of the buttock regions of the user through the bowl opening of the bidet, wherein the first plurality of images is transmitted to the computing device and analyzed with software to identify feces on the user by detecting the absorption spectra of bilirubin compared to skin of the user in white light;

wherein the computing device sends a signal to the means for moving the fluid nozzle in three-dimensions to automatically adjust the nozzle to eject fluid for cleaning any detected feces on the user's genital and rectal areas;

wherein the camera captures a second plurality of images of the illuminated genital, anal, and surrounding areas of the buttock regions of the user through the bowl opening of the bidet, wherein the second plurality of images is transmitted to the computing device and analyzed with software to identify any remaining feces on the user by detecting the absorption spectra of bilirubin compared to skin of the user in white light;

wherein the computing device sends a signal to the means for moving the fluid nozzle in three-dimensions to automatically adjust the nozzle to eject fluid for cleaning any detected remaining feces on the user's genital and rectal areas;

wherein the camera continues capturing additional pluralities of images of the illuminated genital, anal, and surrounding areas of the buttock regions of the user for analysis with the software to identify any remaining feces on the user by detecting the absorption spectra of bilirubin compared to skin of the user in white light until no more feces is identified; and further wherein the computing device sends a signal to the means for moving the air nozzle in three-dimensions to automatically adjust the air nozzles to eject dry air for drying for the user's genital and rectal areas.

9. The electronic bidet system of claim 8, wherein feces are detected by the ratio of green channel light absorbed divided by blue channel light absorbed minus 1, wherein in the absence of feces has a value of zero and the amount of feces increases as the ratio between the green channel light absorbed divided by blue channel light absorbed increases.

10. The electronic bidet system of claim 8, wherein the actuating device comprises a proximity sensor that detects the user sitting on the bidet and automatically activates the bidet.

11. The electronic bidet system of claim 8, wherein the actuating device comprises a proximity sensor that detects the user sitting on the bidet and automatically activates the bidet wherein the proximity sensor consists of a group selected from infrared sensors, weight sensors, and motion detection cameras.

12. The electronic bidet system of claim 8, wherein the fluids emitted by the fluid nozzle consist of a group selected from the combination of clean water rinses, hypoallergenic liquid soaps, and liquids medications.

13. The electronic bidet system of claim 8, wherein the software will identify and locate the anus, testicles, penis, vagina, hair clusters, burn marks, hemorrhoids, birth marks, moles, acne, tumors, and soiled locations of the user.

14. The electronic commode system of claim 8, wherein the first, second, and additional pluralities of images comprise digital video.

15. An electronic wheelchair commode system with artificial intelligence, computer vision, and spectroscopy software comprising:

a re-fillable water reservoir tank;

a bowl with an opening;

a seat;

a seat lid;

at least one fluid nozzle for ejecting fluid;

means on the wheelchair commode for moving the fluid nozzle in three-dimensions within the bowl;

at least one air dryer comprising an air dryer nozzle and means on the wheelchair commode for moving the air dryer nozzle in three-dimensions within the bowl;

a computing device comprising executable software and a memory storage device;

a camera contained within the bowl, wherein the camera is operatively connected to the computing device;

a light source within the wheelchair commode proximate to the camera;

at least one actuating device for activating the wheelchair commode, wherein the activated wheelchair commode illuminates the genital, anal, and surrounding areas of the buttock regions of a user through the bowl opening with the light source with white light;

wherein the camera captures a first plurality of images of the illuminated genital, anal, and surrounding areas of the buttock regions of the user through the bowl opening of the wheelchair commode, wherein the first plurality of images is transmitted to the computing device and analyzed with software to identify feces on the user by detecting the absorption spectra of bilirubin compared to skin of the user in white light;

wherein the computing device sends a signal to the means for moving the fluid nozzle in three-dimensions to automatically adjust the nozzle to eject fluid for cleaning any detected feces on the user's genital and rectal areas;

wherein the camera captures a second plurality of images of the illuminated genital, anal, and surrounding areas of the buttock regions of the user through the bowl opening of the wheelchair commode, wherein the second plurality of images is transmitted to the computing device and analyzed with software to identify any remaining feces on the user by detecting the absorption spectra of bilirubin compared to skin of the user in white light;

wherein the computing device sends a signal to the means for moving the fluid nozzle in three-dimensions to automatically adjust the nozzle to eject fluid for cleaning any detected remaining feces on the user's genital and rectal areas;

wherein the camera continues capturing additional pluralities of the illuminated genital, anal, and surrounding areas of the buttock regions of the user for analysis with the software to identify any remaining feces on the user by detecting the absorption spectra of bilirubin compared to skin of the user in white light until no more feces is identified; and further wherein the computing device sends a signal to the means for moving the air nozzle in three-dimensions to automatically adjust the air nozzles to eject dry air for drying for the user's genital and rectal areas.

16. The electronic wheelchair commode system of claim 15, wherein feces are detected by the ratio of green channel light absorbed divided by blue channel light absorbed minus 1, wherein in the absence of feces has a value of zero and the amount of feces increases as the ratio between the green channel light absorbed divided by blue channel light absorbed increases.

17. The electronic wheelchair commode system of claim 15, wherein the actuating device comprises a proximity sensor that detects the user sitting on the wheelchair commode and automatically activates the wheelchair commode.

18. The electronic wheelchair commode system of claim 15, wherein the actuating device comprises a proximity sensor that detects the user sitting on the wheelchair commode and automatically activates the wheelchair commode wherein the proximity sensor consists of a group selected from infrared sensors, weight sensors, and motion detection cameras.

19. The electronic wheelchair commode system of claim 15, wherein the fluids emitted by the fluid nozzle consist of a group selected from the combination of clean water rinses, hypoallergenic liquid soaps, and liquids medications.

20. The electronic wheelchair commode system of claim 15, wherein the software will identify and locate the anus, testicles, penis, vagina, hair clusters, burn marks, hemorrhoids, birth marks, moles, acne, tumors, and soiled locations of the user.

\* \* \* \* \*